United States Patent
Liu et al.

(10) Patent No.: US 11,255,943 B2
(45) Date of Patent: Feb. 22, 2022

(54) MOTION DETERMINATION FOR VOLUMETRIC MAGNETIC RESONANCE IMAGING USING A DEEP MACHINE-LEARNING MODEL

(71) Applicant: Siemens Healthcare GmbH, Erlangen (DE)

(72) Inventors: LuoLuo Liu, Baltimore, MD (US); Xiao Chen, Princeton, NJ (US); Silvia Bettina Arroyo Camejo, Nuremberg (DE); Benjamin L. Odry, West New York, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 182 days.

(21) Appl. No.: 16/162,559

(22) Filed: Oct. 17, 2018

(65) Prior Publication Data

US 2020/0049785 A1 Feb. 13, 2020

Related U.S. Application Data

(60) Provisional application No. 62/717,968, filed on Aug. 13, 2018.

(51) Int. Cl.
*G06T 7/254* (2017.01)
*G06T 7/246* (2017.01)
(Continued)

(52) U.S. Cl.
CPC ... *G01R 33/56509* (2013.01); *G01R 33/4818* (2013.01); *G06N 3/08* (2013.01);
(Continued)

(58) Field of Classification Search
CPC ..... A61B 5/7207; A61B 5/7203; A61B 34/10; A61B 2034/105; A61B 2090/374;
(Continued)

(56) References Cited

U.S. PATENT DOCUMENTS 9,326,907 B2 * 5/2016 Marle ............... A61G 7/1057
2011/0260726 A1 * 10/2011 Techavipoo ....... G01R 33/5616
324/309

(Continued)

OTHER PUBLICATIONS

Chen et al., Brain MRI super resolution using 3D deep densely connected neural networks, Apr. 4-7, 2018 [retrieved Jun. 5, 2020], 2018 IEEE 15th International Symposium on Biomedical Imaging, pp. 739-742. Retrieved: https://ieeexplore.ieee.org/abstract/document/8363679 (Year: 2018).*

(Continued)

*Primary Examiner* — Matthew C Bella
*Assistant Examiner* — Dennis Rosario (57) ABSTRACT

For determination of motion artifact in MR imaging, motion of the patient in three dimensions is used with a measurement k-space line order based on one or more actual imaging sequences to generate training data. The MR scan of the ground truth three-dimensional (3D) representation subjected to 3D motion is simulated using the realistic line order. The difference between the resulting reconstructed 3D representation and the ground truth 3D representation is used in machine-based deep learning to train a network to predict motion artifact or level given an input 3D representation from a scan of a patient. The architecture of the network may be defined to deal with anisotropic data from the MR scan.

19 Claims, 3 Drawing Sheets

(51) Int. Cl.
  *G01R 33/565* (2006.01)
  *G06N 20/00* (2019.01)
  *G01R 33/48* (2006.01)
  *G06N 3/08* (2006.01)
  *G06T 11/00* (2006.01)

(52) U.S. Cl.
  CPC ............. *G06N 20/00* (2019.01); *G06T 7/251* (2017.01); *G06T 7/254* (2017.01); *G06T 11/008* (2013.01)

(58) Field of Classification Search
  CPC ................ A61B 5/055; G01R 33/5611; G01R 33/5608; G01R 33/50; G01R 33/4818; G01R 33/56341; G01R 33/5616; G01R 33/56; G01R 33/56509; G06T 2207/10088; G06T 7/0012; G06T 2207/20081; G06T 2207/20084; G06T 11/006; G06T 11/008; G06T 2210/41; G06T 11/003; G06T 2207/30004; G06T 2207/30048; G06T 7/20; G06T 7/0016; G06T 2207/30104; G06T 7/251; G06T 7/254; G06N 3/0454; G06N 3/08; G06N 20/00; G06N 3/02
  See application file for complete search history.

(56) References Cited

U.S. PATENT DOCUMENTS

2017/0285122 A1* 10/2017 Kaditz .................. G01R 33/448
2019/0370638 A1* 12/2019 Green .................... G06N 3/084
2021/0225047 A1* 7/2021 Pawar ................ G01R 33/4818

OTHER PUBLICATIONS

Zhang et al., Automatic Segmentation of Acute Ischemic Stroke From DWI Using 3-D Fully Convolutional DenseNets, Mar. 30, 2018 [retrieved Jun. 5, 2020], IEEE Transactions on Medical Imaging, vol. 37, Issue:9, pp. 2149-2160. Retrieved: https://ieeexplore.ieee.org/stamp/stamp.jsp?tp=&arnumber=8328863 (Year: 2018).*
Engstrom et al., Collapsed fat navigators for brain 3D rigid body motion, Oct. 2015 [retrieved Jun. 5, 2020], Magnetic Resonance Imaging, vol. 33, Issue 8, pp. 984-991. Retrieved: https://www.sciencedirect.com/science/article/pii/S0730725X15001599 (Year: 2015).*
Loktyushin, Alexander, et al. "Blind retrospective motion correction of MR images." Magnetic resonance in medicine 70.6 (2013): 1608-1618.
Loktyushin, Alexander, et al. "Retrospective motion correction of magnitude-input MR images." Medical Learning Meets Medical Imaging. Springer, Cham, 2015.
Liu, Siqi, et al. "3d anisotropic hybrid network: Transferring convolutional features from 2d images to 3d anisotropic volumes." International Conference on Medical Image Computing and Computer-Assisted Intervention. Springer, Cham, 2018.
B. Odry, et al. "Improved hemorrhage detection on non contrast head CT using a robust artificial intelligence pipeline," ASNR 56th Annual Meeting, Vancouver, Canada, 2018.
Kober, Tobias, et al. "Head motion detection using FID navigators." Magnetic resonance in medicine 66:135-143 (2011).
Meding, Kristof, Alexander Loktyushin, and Michael Hirsch. "Automatic detection of motion artifacts in MR images using CNNS." Acoustics, Speech and Signal Processing (ICASSP), 2017 IEEE International Conference on. IEEE, 2017.
Mortamet, Bénédicte, et al. "Automatic quality assessment in structural brain magnetic resonance imaging." Magnetic Resonance in Medicine: An Official Journal of the International Society for Magnetic Resonance in Medicine 62.2 (2009): 365-372.
S. Braun, et al. "Motion Detection and Quality Assessment of MR images with Deep Convolutional DenseNets" Medical Imaging Technologies, Siemens Healthineers, Princeton, NJ, United States. Accessed Oct. 4, 2018.

* cited by examiner

MOTION DETERMINATION FOR VOLUMETRIC MAGNETIC RESONANCE IMAGING USING A DEEP MACHINE-LEARNING MODEL

RELATED APPLICATIONS

The present patent document claims the benefit of the filing date under 35 U.S.C. § 119(e) of Provisional U.S. Patent Application Ser. No. 62/717,968, filed Aug. 13, 2018, which is hereby incorporated by reference.

BACKGROUND

The present embodiments relate to scoring a magnetic resonance (MR) reconstruction for image quality due to motion, chemical shift, eddy current, or other sources. Patient motion during MR scanning is one common source of MR artifacts and may lead to blurring, ghosting and distortion in MR images. To ensure sufficient quality of the acquired data, quality assessment is implemented in the imaging pipeline. A scoring system assesses quality and helps determine whether enough significant clinical value may be extracted and therefore lead to correct diagnosis.

Traditional approaches to assess motion artifact severity in MR images include tracking sensors and analyzing the air background. With the rise of deep learning methods, several studies have trained end-to-end neural networks that perform regression from two-dimensional (2D) images to image quality scores directly. 2D image quality and in-plane 2D motion have been simulated and quality scores given based on individual 2D image slices. In practice, the real patient motion is in three dimensions, so 2D image-based scoring and simulation may be inaccurate. Volumetric (multi-slice) MR imaging is commonly practiced, so scoring the final 2D image may not accurately reflect artifact from motion.

SUMMARY

By way of introduction, the preferred embodiments described below include methods, systems, and instructions in non-transitory computer readable media for determination of artifacts in MR imaging. Motion of the patient in three dimensions is used with a measurement k-space line order based on one or more actual imaging sequences to generate training data. The MR scan of the ground truth three-dimensional (3D) representation subjected to 3D motion is simulated using the realistic line order. The difference between the resulting reconstructed 3D representation and the ground truth 3D representation is used in machine-based deep learning to train a network to predict motion artifacts given an input 3D representation from a scan of a patient. The architecture of the network may be defined to deal with anisotropic data from the MR scan.

In a first aspect, a method is provided for machine learning to determine motion artifacts for a magnetic resonance system. The magnetic resonance system generates a first three-dimensional representation of a patient. The three-dimensional representation is reoriented over the scan time based on a model of motion. Magnetic resonance scanning of the patient from the reoriented three-dimensional representation over time is simulated. The simulation of the magnetic resonance scanning includes a line order for k-space measurements where the k-space measurements at different times are simulated from the reoriented three-dimensional representation at different orientations. A second three-dimensional representation is reconstructed from the k-space measurements of the simulated scanning of the three-dimensional representation as reoriented over time. A machine, using deep learning, trains a network to indicate a level of motion artifact based on a difference between the first and second three-dimensional representations. The machine-learned network is stored.

In a second aspect, a method is provided for determining motion artifacts for a magnetic resonance system. A three-dimensional representation of a patient is reconstructed from a magnetic resonance scan of the patient. A level of the motion artifact is determined from a machine-learned network in response to input of the three-dimensional representation to the machine-learned network. The level of the motion artifact is displayed with an image from the three-dimensional representation.

In a third aspect, a method is provided for machine learning to determine motion artifacts. Training data is created from a first magnetic resonance reconstruction from k-space data generated using a scan acquisition order applied to a volumetric-slice magnetic resonance reconstruction subject to motion from a motion model. An error of the first magnetic resonance reconstruction to the volumetric-slice magnetic resonance reconstruction is determined A machine trains a neural network to receive a second magnetic resonance reconstruction from a magnetic resonance scan and to output a score. The training uses the error and the training data. The machine-learned neural network is stored.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Motion assessment via deep learning is provided for volumetric MR images. The motion severity is assed for volumetric MR images (e.g., multi-slice or full 3D) using deep learning. The quality of an MR scan is evaluated based on the whole volume rather than a 2D image from the volume. The deep learning addresses technical challenges in the extension from 2D to multi-slice in the training and network architecture. Challenges include anisotropic spatial resolution in the image slice direction and realistic motion artifacts simulation for training.

The training data is generated based on realistic motion artifacts in multi-slice images. A 3D motion model and a real scan acquisition order are used. Motion is simulated to generate training data pairs where the quality of the images is measured quantitatively and with high throughput. Realistic motion artifacts in multi-slice images are generated using a 3D motion model with various configurable parameters that mimic real-life patient motion for a patient lying on a bed. A practical acquisition scheme from a real MRI scan protocol is used to mimic scanner acquisition given the motion in the simulation. Thus, the impact of the motion to the final images is realistic. Special network structures are proposed to address the anisotropic spatial resolution in the volumetric MR images.

Motion artifact is used in the examples herein. In other embodiments, the severity of other MR artifacts is determined, such as chemical shift or eddy current.

Figure 1:
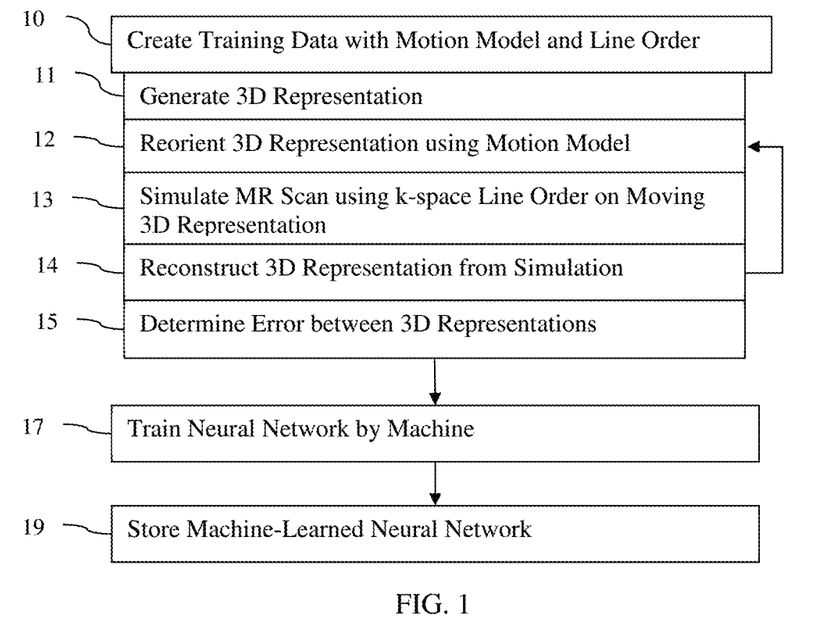
FIG. 1 is a flow chart diagram of one embodiment of a method for machine learning to determine motion artifact level.

FIG. 1 is a flow chart diagram of one embodiment of a method for machine learning to determine motion artifact. Machine learning is used to determine motion artifact for a magnetic resonance system. Given a 3D reconstruction from a particular patient, the machine learns to indicate the level of motion distortion. To create the training data, 3D motion of the patient and the interaction of the line order of the MR scan are simulated, resulting in the machine learning more accurately or resulting in a better way to indicate the level of motion for a given patient. This level of motion may be used to determine whether an MR reconstruction is diagnostically useful.

The method is implemented by a machine, such as a computer, workstation, server, or other processing component, with access to a database of hundreds or thousands of examples of 3D representations (e.g., 3D reconstruction or multi-slice imaging data). The quality of each example 3D representation is based on the 3D representation without motion and a reconstruction from the simulation with motion. The machine learns to determine the quality using the examples and corresponding ground truth qualities.

The acts are performed in the order shown (numeric or top-to-bottom), but other orders may be used. Additional, fewer, or different acts may be provided. For example, acts 11-15 are one embodiment for implementing act 10. Other acts or combinations of acts may be used to create the training data. As another example, act 19 is not provided. In yet another example, acts for application of the machine-learned network are provided, such as the acts of FIG. 6.

In act 10, the machine creates training data. For each example in the training data, a ground truth scan of a patient, phantom, or other object with little or no motion is used. Alternatively, acquiring images or scan data post-processed to minimize or reduce motion artifacts are used. The ground truth scan is a multi-slice, volume, and/or another 3D MR reconstruction. This MR reconstruction is subjected to motion from a motion model, such as 3D motion based on modeling a person moving while lying on a bed of the MR scanner. Using a scan acquisition order, the 3D representation is created by simulating MR scan and MR reconstruction as if the patient were moving during the scan. A difference between the ground truth scan and the reconstruction from the simulation indicates the level of motion effect in the 3D MR reconstruction. The reconstructed 3D representation from the simulation and the difference are used as the training data.

Acts 11-15 show one embodiment for creating the training data. Other embodiments may be used. One of the many examples used in training is generated. The example includes a 3D MR representation subjected to motion and an output ground truth, such as an error, level, difference, or amount of motion artifact.

In act 11, a magnetic resonance system generates a 3D representation of a patient. A medical MR scanner generates an image representing a patient. The image is made available by or within the medical scanner. The medical image or dataset is acquired by the medical MR scanner. Alternatively, the acquisition is from storage or memory, such as acquiring a previously created dataset from a PACS. A processor may extract the data from a picture archive communications system or a medical records database. Acquisition may be through transmission over a network.

The image is medical imaging MR data. The medical image is a frame of data representing a volume of the patient. The data may be in any format. While the terms image and imaging are used, the image or imaging data may be in a format prior to actual display of the image. For example, the medical image may be a plurality of scalar values representing different locations in a Cartesian, radial, spiral, or polar coordinate format different than a display format. The image or imaging is a dataset that may be used for imaging, such as scan data representing the patient.

MR data representing a patient is acquired. MR data is acquired with an MR system. The data is acquired using a pulse sequence for scanning a patient. Data representing an interior region of a patient is acquired. A pulse sequence and corresponding sampling line order is used to measure, resulting in k-space data representing a volume of the patient. Helical (spiral), Cartesian, rotational (radial), or another scan pattern is used. The k-space data is then reconstructed. Fourier analysis on k-space measurements is performed to reconstruct the data from the k-space into a 3D object or image space.

The medical image represents tissue and/or bone structure of the patient. Alternatively, the medical image represents flow, velocity, or fluids within the patient. In other embodiments, the medical image represents both flow and structure.

The medical image represents a 3D region of the patient. For example, the medical image represents multiple parallel planes or slices of the patient. A volume may be represented as slices with pixel values or as voxels in 3D. Values are provided for each of multiple locations distributed in three dimensions. The medical image is acquired as a frame of data.

The frame of data represents the scan region based on measurements made over time following the scan line order or sequence. For example, each measurement is along a line with 256 sample locations. Such lines are measured orthogonal to a 256×256 sample plane. The order of the sampling over the 256×256 sample plane may be sequential (e.g., line by line over a plane, then line by line over a next plane . . . ) or non-sequential (e.g., measuring along inner sample locations or lines prior to outer). Any number of planes may be used, such as 64. Groups of lines may be measured in response to a same pulse, so measurements may be in any order of group of lines by group of lines.

The combination of motion and scan line order may result in the occurrence of a motion artifact. The 3D representation acquired in act 11 is acquired to have little or no motion artifact. For example, a phantom is used. As another example, a sleeping patient or patient with little movement is scanned.

The 3D representation is used to create another 3D representation subjected to motion. Since many examples are to be made with different motion and/or scan line orders, acquiring data from patients for the many different examples is possible, but unpractical. Instead, the 3D representation is used with MR scan simulation to create examples of different motion and/or scan line orders.

In act 12, the machine reorients the 3D representation over time based on a model of motion. The motion is defined in 3D. Any number of parameters may define the model of motion. For example, rotation about each of three orthogonal axes. Rotation about each axis may be defined by range of motion, frequency (e.g., speed), and/or variation in range and/or speed. Periodic or non-periodic motion may be used. The motion model may include no, one, or more periods of no motion as part of the motion schedule. The motion model schedules the motion for a given example. Different motion schedules may be used for different examples.

The motion may be applied to any body part or the entire patient. One implementation used herein includes periodic and non-periodic head shakings. Other implementations may be for arm, hand, leg, foot, head, and/or torso motion.

The motion is based on a patient lying on a bed during the scan. Rather than rotating about a center axis in the patient, the rotation is about a back of the head at the patient bed. A head of the patient is reoriented about an axis of rotation tangential to a back of the head. The axis may be a longitudinal axis to the patient on a surface of a bed. The motion model assumes 3D pivoting motion along a longitudinal axis tangential to the back of the head. Motions for other body parts are relative to the patient bed or as constrained movement based on the bed or MR scanner.

Figure 2A:
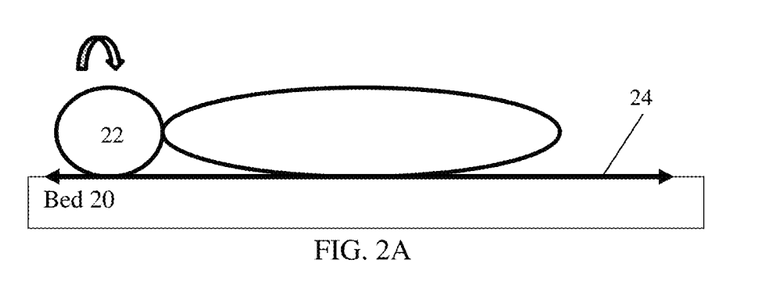
FIGS. 2A and 2B are cross-section views along orthogonal planes shows modeled patient motion in 3D.
Figure 2B:
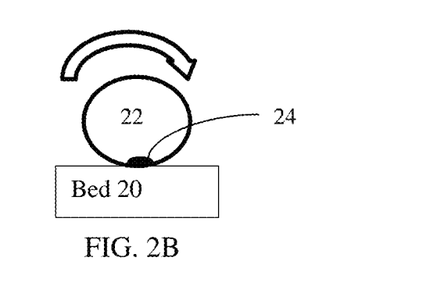

The reorientation is of the 3D representation. For example, FIGS. 2A and 2B show the head 22 rotating about a longitudinal axis 24 on the patient bed 20. Based on segmentation or user designation of the axis of rotation, the 3D representation is rotated about the axis 24. Where the 3D representation is of only or mostly the head 22, then the entire 3D representation is rotated. Where the torso is included, then the part representing the head 22 is rotated while the part representing the torso is not. Alternatively, the entire 3D representation is rotated. The rotation is rigid. Alternatively, non-rigid motion may be used.

The reorientation changes over time. Based on the values of the parameters of the motion model, the 3D representation is moved relative to a simulated MR scanner in an ongoing manner.

In act 13, the machine simulates MR scanning of the patient from the reoriented three-dimensional representation over time. Any MR simulation may be used, such as JEMRIS, MRiLab, or a pipeline to convert images into k-space, merge k-space data, and then convert the k-space data into images, including consideration of multi-coil acquisition. The 3D representation as oriented at a given time provides scalar values for locations in the volume for simulating the MR scan.

The simulation includes the line order for k-space measurements. At a given time, a given line or group of lines are measured. The 3D representation as oriented at that time is used to determine the k-space measurements for the line or group of lines. The k-space readout is assumed to be fast enough to freeze motion within a k-space readout line. As the sequence of lines is measured, the 3D representation moves so that the orientation is different for different measurement lines of the line order. The k-space measurements at different times are simulated from the reoriented 3D representation at different orientations. Due to the time between measurements in the line acquisitions, the k-space line acquisition order impacts on the final motion artifact appearance.

Any line order may be used. For different applications, different line orders are used. By using a line order from an actual or realistic MR acquisition protocol, the resulting motion artifacts may be more like actual motion artifacts. In one embodiment, the line order is from a default scan protocol for scanning patients. An actual protocol for a given application is used, such as an MR acquisition protocol used for various patients and/or on multiple MR scanners at medical facilities. A clinically appropriate (e.g., approved or tested) line order is used. The acquisition order is extracted from a real scan protocol.

Due to the use of an actual protocol, the line order may not be sequential (i.e., is non-sequential). For example, a 256×256×64 volume is scanned in a Cartesian format. A first plane includes 256 lines, numbered 0-255, a next adjacent plane includes 256 lines numbers 256-510, . . . for 64 sequential planes. The lines may be measured in numerical order or a different order. By measuring in a different order, a non-sequential line order is provided (e.g., measuring lines 280-320, then 0-50, then . . . ). Any order may be used. The order may be based on clinical testing and/or other development of a protocol to scan patients for a given application or applications. Sequential line order may be used.

The line order for an actual scan protocol may be at a different resolution than desired. For example, the desired resolution is 128×128×32. A scan protocol of a different resolution may be used. The pattern of the line order is maintained (e.g., every odd line, then every even line) but the line order is adjusted for the number of lines. The line order is adjusted according to the image size, such as decimating by a factor of 2 while keeping the pattern of line placement order.

The simulation provides k-space measurements as if the object represented by the 3D representation while undergoing motion defined by the motion model were scanned with MR. The k-space measurements include variation due to the motion imparted to the 3D representation according to the motion model.

In act 14, the machine reconstructs a 3D representation from the k-space measurements of the simulated scanning of the 3D representation as reoriented over time. A fast Fourier or other transform is applied to determine a multi-slice or other 3D representation from the simulated k-space measurements. Any MR reconstruction may be used. The reconstructed 3D representation is different than the original 3D representation due to the motion interaction with the line order.

The feedback from act 14 to act 12 represents creation of other examples. A range of motion severity may be obtained by adjusting motion model parameters and/or acquisition orders. The value or values of one or more parameters of the motion model are changed to create other examples. The reorienting of act 12 is performed using the different value or values. The corresponding simulation of act 13 and reconstruction of act 14 result in a different example using the same starting 3D representation but with different motion. Many examples of simulated 3D representations may be provided from the different motions.

Using the same or different motion, the line order may be changed. Using a different line order allows simulation and reconstruction to be repeated to create another example 3D representation. Another actual line order may be used. Alternatively or additionally, the line order is perturbed. The perturbation may follow a pattern, such as flipping or exchanging different lines with each other in the order. The perturbation may be randomized, such as applying a randomization to one or more line or groups of lines in the order. Many examples may be provided with different line orders.

Using line order and/or motion change, many examples of reconstructed 3D representations of act 14 are formed using the same 3D representation of act 11. Other examples may be generated by using repetition of act 11, thus providing one or more different 3D representations to be used for adding motion and simulating.

In act 15, the machine determines an error for each example. The distance between an MR reconstruction to another MR reconstruction (e.g., with and without motion artifact) is determined with respect to a suitable distance metric. The resulting distance is referred to as error. The reconstructed 3D representation with the motion artifact is compared to the 3D representation with little or not motion artifact (e.g., the multi-slice MR reconstruction from act 11 is compared with the multi-slice MR reconstruction from act 14). For machine training, a ground truth measure of the effect of motion and/or line order relative to motion is determined. To train the network to assess the quality with a score, a target quality score is determined as the ground truth for the machine training.

Due to the availability of motion-free images, metrics such as root mean square error, structural similarity etc. may be used. In one embodiment, the score or image quality metric is a normalized root mean squared error (NRMSE) between the simulated and the original image stacks. The error or measure of difference between the 3D representations is used as the ground truth for machine training. Alternatively, the error may be adjusted or used in a function to provide the score used in training as the ground truth.

In act 17, the machine trains a network to indicate a level of motion artifact. The same or different machine used to create the training data is used to train. For example, one or more workstations generate the training data (e.g., 3D representations reconstructed from the simulations and the level of motion artifact for each). One of the workstations or a different processor (e.g., server) trains using machine learning from the examples, which are stored in a database or other memory.

The training is based on a difference between the starting 3D representation or representations and the 3D representations reconstructed from the simulation with motion. The machine learns to determine a score (e.g., difference) based on input of a 3D representation from a scan of an actual patient. The 3D representation is subjected to motion of the patient, so the machine is trained to output a score based on knowledge gleaned or regressed from the training data (e.g., determined errors of the training data). The training is based on results from the repetitions.

Any machine learning may be used. In one embodiment, deep learning is used. Using a piecewise-differentiable function or other deep learning function, the machine trains a network to output a score in response to an input image. Support vector machine, Bayesian network, probabilistic boosting tree, neural network, sparse auto-encoding classifier, or other now known or later developed machine learning may be used. Any semi-supervised, supervised, or unsupervised learning may be used. Hierarchal, cascade, or other approaches may be used.

In one embodiment, a neural network (e.g., deep neural network) is used. Other deep learned, sparse auto-encoding classifiers may be trained and applied. The machine training is unsupervised in learning the features to use and how to classify given the learned feature vector. A deep neural network is trained to estimate with a $L_2$ loss (e.g., least squares error) or other loss to obtain optimal network parameters. The difference between the ground truth or known scores for the training images (e.g., examples of 3D representations) and the predictions by the network is minimized.

The network is trained with training data. Samples of input data with ground truth are used to learn to classify the score. For deep learning, the classifier learns the features of the input data to extract from the training data. Alternatively, the features, at least for the input, are manually programmed, such as filtering the scan data and inputting the results of the filtering. The training relates the input data to the classification through one or more layers. One layer may relate feature values to the class. For deep-learned networks, there may be further layers creating further abstract features from outputs of pervious layers. The resulting machine-trained classifier is a matrix for inputs, convolution kernels, down-sampling, weighting, and/or combination to output a classification and/or probability of class membership. The deep machine-trained network includes two or more layers relating the input to the class.

Since 3D MR often results in anisotropic data, the network architecture is defined to address this unequal distribution of data. For example, 64 slices or planes are reconstructed with 256×256 sample resolution. The resolution along the slice direction is different than the in-plane resolution. The network is designed to accept anisotropic data, such as including anisotropic convolution kernels and/or anisotropic down sampling. Alternatively, anisotropic data is input to the network, which derives features and classifies without design specific to anisotropic data. In yet other alternatives, the 3D representation is up or down sampled anisotropically to generate an isotropic 3D representation to be used as the input. Any other network architecture may be used.

Figure 3:
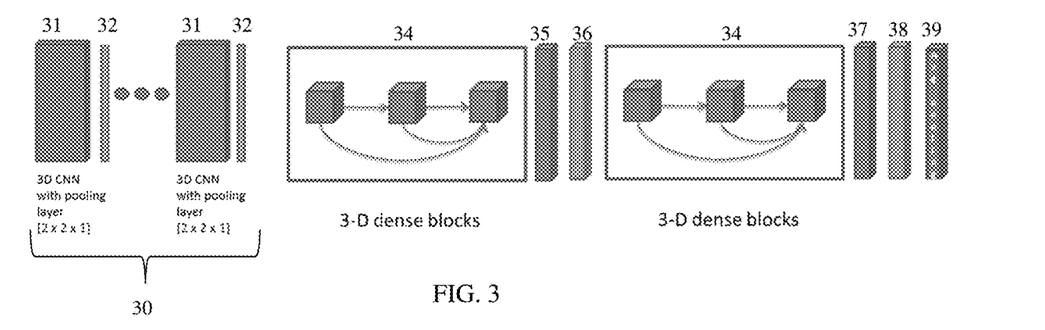
FIGS. 3-5 show different embodiments of network architectures for machine learning to score motion artifact level in 3D MR.

FIG. 3 illustrates one embodiment of a network architecture of a neural network for input of anisotropic multi-slice 3D representation. A cascade 30 of 3D convolution and pooling layers (31, 32) with anisotropic kernels and down sampling output isotropic features to 3D dense blocks 34. A 3D network FlexNet is used with adaptation for anisotropic data. The cascade of anisotropic kernels and dense blocks is used for training an end-to-end model from input volumes to a quality score. Several layers of 3D convolutional neural networks 31 with uneven-sized convolution and pooling layers 32 with uneven down sampling generate feature maps that have similar sizes at all dimensions (e.g., isotropic). These features are cascaded to 3D dense blocks 34. The 3D dense blocks 34 include various layers, such as fully connected layers, with one or more skip connections to a final fully connected layer. The 3D dense blocks 34 output to a 3D convolution layer 35, followed by a 3D pooling layer 36. The 3D pooling layer 36 outputs to another 3D dense blocks 34, which outputs to a 3D convolution layer 37. The 3D convolution layer 37 outputs to a pooling layer 38, which outputs to an average pooling or other combination layer 39 for outputting the score. Additional, different, or fewer layers may be used. Based on input of examples of multi-slice, motion-corrupted volumes with associated volume quality indices, this network may be trained to output a score given an input multi-slice, motion-corrupted 3D representation of a patient.

Figure 4:
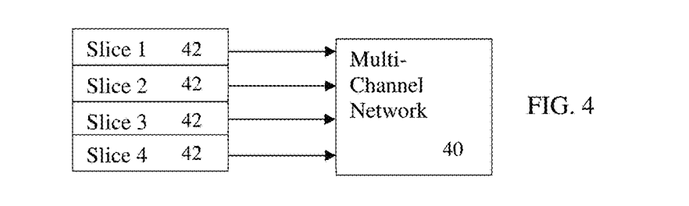

FIG. 4 shows another example network for input of anisotropic 3D representation. A multi-channel 2D network 40 is used. Each channel receives 2D input data. An input channel is provided for each slice 42, such as 64 input channels for 256×256 data. The slices 42 are treated as features of the input volume and are input as channels to the network 40. One implementation includes a multi-channel 2D (MC2D) network 40 composed of a fully-connected convolutional layer and three 2D dense blocks. Other MC2D networks may be used.

Figure 5:
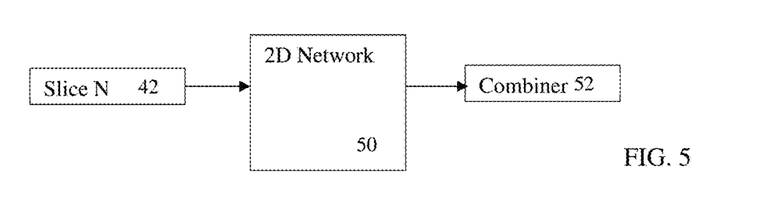

FIG. 5 shows yet another example network for input of anisotropic 3D representation. A 2D network 50 includes convolution, pooling, dense, and/or other layers in any arrangement. The 2D network operates with 2D inputs to output a score. The image quality (e.g., level of motion artifact) for a given slice 42 is determined. The slices 42 are input sequentially, resulting in a sequence of scores for the various slices 42. The network 50 is trained to assess image quality for a 2D slice. Quality scores are provided for each or a sub-set of slices 42. A combiner 52 combines the scores, merging the quality scores or features into a single output metric. For example, the scores are averaged, or a median is selected.

Other neural networks or network architectures may be used. The network is trained to output a score of image quality. Any scoring may be used. For example, a numerical range representing quality is provided, such as 1-5 or 1-10, where the larger or smaller number represents highest quality or lowest motion artifact. As another example, alphanumeric classes are used, such as poor or good or such as poor, below average, average, good, or excellent.

The network is trained to assign the class based on the input 3D representation. For deep learning, the network learns features to extract from the input and learns to relate values of the features to the class (i.e., score, such as NRMSE). In additional or alternative embodiments, manually programmed features (e.g., Haar wavelets, steerable features, maximum detection) are extracted and used as the input feature vector.

After creation, the machine-learned network includes one or more layers with values for various parameters, such as convolution kernels, down sampling weights, and/or connections. The values of the parameters and/or the network as trained are stored in act 19. The machine-learned network is stored in a memory, such as memory of the machine or the database with the examples. The machine-learned network may be transmitted to a different memory. The machine-learned neural network may be duplicated for application by other devices or machines, such as processors of MR scanners. The memories of MR scanners may store copies of the machine-learned network for application for specific patients, enabling a radiologist or other physician to determine whether to rely on an image or to scan again for diagnosis due to patient motion.

Figure 6:
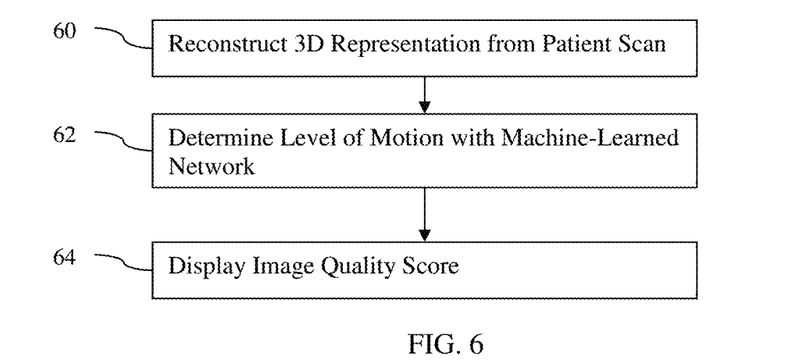
FIG. 6 is a flow chart diagram of one embodiment of a method for determining motion artifact level with a machine-learned network.

FIG. 6 is a flow chart diagram of one embodiment of a method for determining motion artifact for a magnetic resonance system. The stored machine-learned network is applied to determine a score for a scan of a patient. A 3D scan of the patient is performed, and the level of motion artifact from the resulting 3D representation of that patient is determined by the machine-learned network.

An MR scanner scans the patient. The MR scanner, the system of FIG. 7, a server, or other machine determines the level of motion and outputs the score to a display device.

Additional, different, or fewer acts may be provided. For example, the score is output to a memory (e.g., computerized medical record) instead of displayed in act 64. The acts are performed in the order shown (top to bottom), but other orders may be used.

In act 60, an MR scanner reconstructs a 3D representation of a patient from an MR scan of the patient. The image is made available by or within the medical scanner. The medical image or dataset is acquired by the medical scanner using a scan protocol. Alternatively, the acquisition is from storage or memory, such as acquiring a previously reconstructed dataset from a PACS. Acquisition may be through transmission over a network.

MR data representing a patient is acquired. MR data is acquired with an MR system or scanner. The data is acquired using a pulse sequence and line order for scanning a patient. Data representing an interior region of a patient is acquired. For MR, the magnetic resonance data is k-space data. Fourier analysis is performed to reconstruct the data from the k-space into a 3D object or image space. The medical image represents tissue and/or bone structure of the patient. Alternatively, the medical image represents flow, velocity, or fluids within the patient. In other embodiments, the medical image represents both flow and structure.

The medical image represents a 3D region of the patient. For example, the medical image represents a plurality of slices of the patient. A 3D distribution of voxels based on the scan pattern or as interpolated to a 3D grid are provided. Values are provided for each of multiple locations distributed in three dimensions.

The image may include motion artifacts. The patient may move during the scan, such as moving their head. The result is noise or blur in the 3D representation. Any level of artifact may exist. The amount of movement, interaction with the line order used, and/or other factors may contribute to different levels of motion artifact.

In act 62, the MR scanner, server, workstation, computer, or other processor determines a level of the motion artifact or another measure for the motion-artifact severity. The 3D representation is input to the machine-learned network. In response to input, the machine-learned network outputs a measure of the level of the motion artifact.

The machine-learned network has an architecture for dealing with the 3D representation being anisotropic. For example, the network is a cascade of 3D convolution and pooling layers with anisotropic kernels and down sampling where the cascade outputs isotropic features to 3D dense blocks. As another example, the network is a multi-channel network for receiving and operating on 2D inputs for each channel. In yet another example, the network is a 2D network for generating scores based on 2D inputs, where the scores from multiple parts of the 3D representation input as 2D sub-sets (e.g., input by slice) are combined to indicate the level of motion artifact.

In addition to outputting the score, the network may output additional information. A probability of class membership may be output (e.g., 75% likelihood of being good quality and 25% likelihood of being poor quality).

In act 64, the processor or MR scanner uses a display device to display the level of the motion artifact. The quality score is transmitted over a network, through a communications interface, into memory or database (e.g., to a computerized patient medical record), or to a display.

In one embodiment, the image quality score ranges from 1 to 5, from best to worst. The score is based on the presence of motion artifacts. The extent and/or severity of motion artifacts throughout the 3D representation may be reflected in the score.

In another embodiment, the score is displayed with an image of the patient. A 2D image is generated by 3D rendering of the 3D representation. Alternatively, a 2D image from a 2D slice or interpolated from a plane in the volume is displayed. The image quality score is displayed with the 2D image of the patient. The score is an annotation, part of a pop-up, in a report, or part of a notice.

The user or the medical scanner uses the quality score. A sufficiently good quality 3D representation (e.g., score or value above or below a threshold) allows for diagnosis with lest risk for error. A poor-quality 3D representation due to the combination of patient motion with the line order may not be sufficient for diagnosis, so the patient is scanned again. An automatic trigger based on score to scan by the MR scanner may be used. Alternatively, the user triggers the subsequent scan based on the score. Once the quality score for motion artifact in an MR image volume is predicted, the operator of the medical scanner or the medical scanner decides whether to rescan the patient. The score is used for a decision to use or not use the generated 3D representation. The result is that a later physician review is more likely to have a useful image for diagnosis, and rescanning is avoided where possible. The score may be used to weight an amount of trust in diagnosis based on a 3D representation reconstructed from a scan of the patient.

Figure 7:
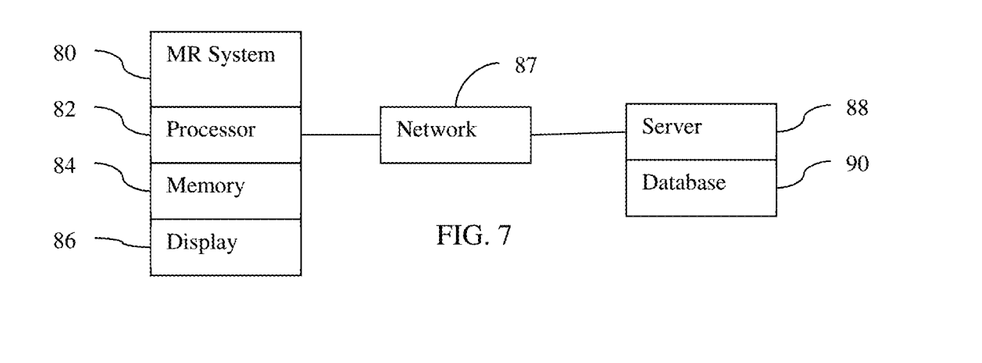
FIG. 7 is a block diagram of one embodiment of a system for machine learning and/or for use of a machine-learned network for image quality scoring in 3D MR due to motion.

FIG. 7 shows one embodiment of a system for machine learning and/or for application of a machine-learned network. The system is distributed between the imaging system 80 and a remote server 88. In other embodiments, the system is just the server 88 or just the imaging system 80 without the network 87. In yet other embodiments, the system is a computer or workstation.

The system includes an imaging system 80, a processor 82, a memory 84, a display 86, a communications network 87, a server 88, and a database 90. Additional, different, or fewer components may be provided. For example, network connections or interfaces are provided, such as for networking with a medical imaging network or data archival system. In another example, a user interface is provided. As another example, the server 88 and database 90 are not provided, or only the server 88 and database 90 are provided. In other examples, the server 88 connects through the network 87 with many imaging systems 80 and/or processors 82.

The processor 82, memory 84, and display 86 are part of the medical imaging system 80. Alternatively, the processor 82, memory 84, and display 86 are part of an archival and/or image processing system, such as associated with a medical records database workstation or server, separate from the imaging system 80. In other embodiments, the processor 82, memory 84, and display 86 are a personal computer, such as desktop or laptop, a workstation, or combinations thereof. The processor 82, display 86, and memory 84 may be provided without other components for acquiring data by scanning a patient.

The imaging system 80, processor 82, memory 84 and display 86 are provided at a same location. The location may be a same room, same building, or same facility. These devices are local relative to each other and are remote relative to the server 88. The server 88 is spaced apart by the network 87 by being in a different facility or by being in a different city, county, state, or country. The server 88 and database 90 are remote from the location of the processor 82 and/or imaging system 80. The database 90 may be local to the processor 82.

The imaging system 80 is a medical diagnostic imaging system. The imaging system 80 is an MR system. The MR system includes a main field magnet, such as a cryomagnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data based on a line order. The received k-space data is converted into object or image space data with Fourier processing.

The memory 84 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 84 is part of the imaging system 80, part of a computer associated with the processor 82, part of a database, part of another system, a picture archival memory, or a standalone device.

The memory 84 stores medical imaging data representing the patient, weights or values of parameters making up some of the layers of the machine-learned network, motion model parameters, orientations, outputs from different layers, one or more machine-learned networks, 3D representations, scores (e.g., error metric or differences relating an amount of motion artifact), and/or 2D images. The memory 84 may store data during processing for application and/or may store training data (e.g., 3D representations from MR simulation using motion from a motion model and scores) and data during processing for machine learning.

The memory 84 or other memory is alternatively or additionally a non-transitory computer readable storage medium storing data representing instructions executable by the programmed processor 82 for training or use of a machine-learned classifier in medical MR imaging. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 82 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for machine training or applying a machine-learned network. The processor 82 is a single device or multiple devices operating in serial, parallel, or separately. The processor 82 may be a main processor of a computer, such as a laptop or desktop computer, or may be a processor for handling some tasks in a larger system, such as in the imaging system 80. The processor 82 is configured by instructions, design, hardware, and/or software to perform the acts discussed herein.

The processor 82 is configured to perform the acts discussed above for training or application. For training, the processor 82 or another processor (e.g., the server 88) generates examples by simulating MR scan of an object represented in 3D undergoing motion defined by a motion model. The processor 82 uses machine learning based on the stored and/or created training data and a defined network architecture. For application, the processor 82 uses a stored machine-learned network. A 3D representation of a given patient from the MR system 80, the memory 84, or the database 90 is input to the machine-learned network, which outputs the score for motion artifact for that 3D representation of that given patient.

The processor 82 is configured to transmit the score for quality due to motion in MR scanning over the network 87, to the display 86, or to the memory 84. The processor 82 may be configured to generate a user interface for requesting and/or presenting the score with or without one or more images generated from the 3D representation.

The display 86 is a monitor, LCD, projector, plasma display, CRT, printer, or other now known or later developed devise for outputting visual information. The display 86 receives images, graphics, text, quantities, or other information from the processor 82, memory 84, imaging system 80, and/or server 88. One or more medical MR images are displayed. The MR images are of a region of the patient. The image includes an indication, such as a graphic or colorization, of the classification results, such as the score. The score may be displayed as the image without a medical MR image of the patient.

The network 87 is a local area, wide area, enterprise, another network, or combinations thereof. In one embodiment, the network 87 is, at least in part, the Internet. Using TCP/IP communications, the network 87 provides for communication between the processor 82 and the server 88. Any format for communications may be used. In other embodiments, dedicated or direct communication is used.

The server 88 is a processor or group of processors. More than one server 88 may be provided. The server 88 is configured by hardware and/or software. In one embodiment, the server 88 performs machine learning with training data in the database 90. The machine-learned network is provided to the processor 82 for application. The results of classification may be received from the processor 82 for use in further training. Alternatively, the server 88 performs the application on an image received from the imaging system 80 and provides the score to the imaging system 80.

The database 90 is a memory, such as a bank of memories, for storing training data, such as 3D representations reconstructed from simulation and respective scores. Weights or values of parameters of machine-learned network are stored in the database 90 and/or the memory 84.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for machine learning to determine severity of motion artifacts on volumetric images of a magnetic resonance system, the method comprising:
generating, by the magnetic resonance system, a first three-dimensional representation of a patient;
reorienting the three-dimensional representation over time based on a model of motion of the patient including three-dimensional motion of the patient from the model of motion of the patient;
simulating magnetic resonance scanning of the patient from the reoriented three-dimensional representation over time, the simulating of the magnetic resonance scanning including simulating a line order for k-space measurements where the k-space measurements at different times are simulated from the reoriented three-dimensional representation at different orientations based on the model of motion of the patient;
reconstructing a second three-dimensional representation from the k-space measurements of the simulated scanning of the three-dimensional representation as reoriented over time subject to the three-dimensional motion of the patient from the model of motion of the patient;
training, by a machine using deep learning, a network determining a score indicating a level of motion artifact based on a difference between the first three-dimensional representation and the second three-dimensional representation subject to the three-dimensional motion of the patient, wherein the score is an error metric or difference relating an amount of motion artifact; and
storing the machine-learned network.

2. The method of claim 1 wherein reorienting, simulating, and reconstructing are repeated for different values of parameters of the model of motion of the patient, and wherein training comprises training based on results from the repetitions.

3. The method of claim 1 wherein simulating and reconstructing are repeated for different line orders, and wherein training comprises training based on results from the repetitions.

4. The method of claim 1 wherein reorienting comprises reorienting a head of the patient with an axis of rotation tangential to a back of the head.

5. The method of claim 4 wherein reorienting comprises rotating the head about the axis wherein the axis is a longitudinal axis to the patient on a surface of a bed.

6. The method of claim 1 wherein simulating comprises simulating with the line order from a default scan protocol for scanning patients.

7. The method of claim 1 wherein simulating comprises simulating with the line order being non-sequential.

8. The method of claim 1 wherein simulating comprises simulating with the line order adjusted from another line order to maintain a pattern with a different number of lines.

9. The method of claim 1 wherein training comprises training with the difference being a normalized root mean square error between the first and second three-dimensional representations.

10. The method of claim 1 wherein training comprises training with the network comprising a cascade of three-dimensional convolution and pooling layers with anisotropic kernels and down sampling outputting isotropic features to three-dimensional dense blocks.

11. The method of claim 1 wherein training comprises training with the network comprising a multi-channel network with two-dimensional inputs.

12. The method of claim 1 wherein training comprises training the network as a network operating on two-dimensional inputs to output scores, the difference comprising an average of the scores.

13. A method for determining motion artifact for a magnetic resonance system, the method comprising:
   reconstructing a three-dimensional representation of a patient from a magnetic resonance scan of the patient;
   determining a level of the motion artifact in the three-dimensional representation from a machine-learned network in response to input of the three-dimensional representation to the machine-learned network, the machine learned network trained to output a determined score indicating the level of the motion artifact based on a difference between three-dimensional representations in training data, wherein at least one three-dimensional representation in the training data is subjected to simulated three-dimensional motion based on a motion model and the determined score is an error metric or difference relating an amount of motion artifact; and
   displaying the level of the motion artifact with an image from the three-dimensional representation.

14. The method of claim 13 wherein determining comprises determining with the machine-learned network comprising a cascade of three-dimensional convolution and pooling layers with anisotropic kernels and down sampling, the cascade outputting isotropic features to three-dimensional dense blocks.

15. The method of claim 13 wherein determining comprises determining with the machine-learned network comprising a multi-channel network with two-dimensional inputs.

16. The method of claim 13 wherein determining comprises determining with the machine-learned network operable on two-dimensional inputs to output scores, the level being a combination of the scores.

17. A method for machine learning to determine motion artifact, the method comprising:
   creating training data from a first magnetic resonance reconstruction from k-space data generated using a scan acquisition order applied to a volumetric-slice magnetic resonance reconstruction subject to patient motion from a motion model including three-dimensional motion of the patient motion from the motion model;
   determining an error of the first magnetic resonance reconstruction compared to the volumetric-slice magnetic resonance reconstruction subject to the patient motion from the motion model;
   training, by a machine, a neural network receiving a second magnetic resonance reconstruction from a magnetic resonance scan and determining and outputting a score indicating a level of motion artifact, the training using the training data and the error of the first magnetic resonance reconstruction compared to the volumetric-slice magnetic resonance reconstruction subject to the patient motion from the motion model, wherein the score is an error metric or difference relating an amount of motion artifact; and
   storing the machine-learned neural network.

18. The method of claim 17 wherein creating comprises creating with the patient motion of the motion model being three-dimensional motion constrained to motion of a patient laying on a bed.

19. The method of claim 17 wherein training comprises training the neural network as a cascade of three-dimensional convolution and pooling layers with anisotropic kernels and down sampling, the cascade outputting isotropic features to three-dimensional dense blocks.

* * * * *